US006177001B1

(12) United States Patent
Meyer

(10) Patent No.: US 6,177,001 B1
(45) Date of Patent: Jan. 23, 2001

(54) INTERNALLY CALIBRATED OXYGEN SENSOR, METHOD AND SYSTEM

(75) Inventor: Emilio Meyer, Milan (IT)

(73) Assignee: Panametrics, Inc., Waltham, MA (US)

( * ) Notice: Under 35 U.S.C. 154(b), the term of this patent shall be extended for 0 days.

(21) Appl. No.: 09/096,683

(22) Filed: Jun. 12, 1998

(51) Int. Cl.[7] .......................... G01N 27/409; G01N 27/41

(52) U.S. Cl. ....................... 205/784; 205/784.5; 204/427; 73/1.06

(58) Field of Search ................................ 205/783.5, 784, 205/784.5; 204/427, 424, 425; 73/1.06

(56) References Cited

FOREIGN PATENT DOCUMENTS

71293 * 6/1977 (JP) .
66751 * 5/1980 (JP) .

OTHER PUBLICATIONS

Translation of Patent JP 52–71293, published Oct. 1975, provided by USPTO Translation Branch, Aug. 1999.*
Translation of Patent JP 55–66751, published May 1980, provided by USPTO Translation Branch, Jul. 1999.*
David M. Haaland "Internal–Reference Solid–Electrolyte Oxygen Sensor", Analytical Chemistry, vol. 49, No. 12, (Oct. 1977), pp. 1813–1817.
C. Franx "A Dynamic Oxygen Sensor with Zero Temperature Coefficient", Sensors and Actuators, 7 (1985), pp. 263–270 Month Unknown.
J. Fouletier, et al. "Measurement and Regulation of Oxygen Content in Gases Using Solid Electrolyte Cells. III. Oxygen pump–gauge", Journal of Applied Electrochemistry 5 (1975) 11–120 Month Unknown.

* cited by examiner

*Primary Examiner*—Robert J. Warden, Sr.
*Assistant Examiner*—Kaj K. Olsen
(74) *Attorney, Agent, or Firm*—Nutter, McClennen & Fish, LLP

(57) ABSTRACT

A zirconium oxide shell forms a chamber of fixed volume, and a controller monitors voltage across the shell indicative of difference between inside and outside oxygen levels, applying a signal to pump oxygen. Pumping is effected to empty the chamber, to develop an internal reference, for example by comparison to ambient air, for calibration, and thereafter to substantially continuously null the difference, i.e., to track the oxygen level of a sample environment. Integrated pump current yields a measure of the oxygen added to or removed from the chamber. A suitable material for forming the sensor is a mixture of about 91% zirconium oxide and 9% yttrium oxide, which is formed to shape as a paste or slurry and sintered at about 1400° C., and then platinum coated, for example by a CVD process, to form porous electrodes on each surface. The controller may apply a sequence of current pulses, and check the Nernst cell output indicative of $\Delta P$ across the wall, until $\Delta P=0$. The controller integrates the applied charge, e.g. number and width of pulses. By operating to maintain $\Delta P=0$, leakage drift is avoided, and required relaxation time between readings becomes negligible. Positive and negative pulses may be tallied in a running sum to determine the present reading, and Nernst cell output may be applied as a feed forward signal to the controller, which determines and then applies the number of pulses or amount of charge needed to again null the output, while the processor adds the present differential as a correction to the last stored reading to provide the oxygen level as an immediate output.

20 Claims, 3 Drawing Sheets

EMPTY SENSOR 61
CALIBRATE 62
STORE M. DATA
METER CONSTANTS
Q/P CONVERSION 63
60
100
PUMP TO $\Delta P=0$ 71
COUNT CHARGE
OUTPUT $O_2$ VALUE 72
70
N NEXT READING? 73 Y
81
READ NERNST VOLTAGE
DISPLAY $P+\Delta P$
PUMP TO $\Delta P=0$ 82
80

INTERNALLY CALIBRATED OXYGEN SENSOR, METHOD AND SYSTEM

TECHNICAL FIELD

The present invention relates to sensors, and in particular, to oxygen sensors used for detecting the level of oxygen present in a gaseous environment.

These sensors employ a thin layer of oxide material, typically zirconia, which is electroded on opposed sides of the layer and, in a typical mode of operation, acts as a Nernst cell. The sensors are operated at an elevated temperature of at least approximately 700° C. which provides a suitably increased level of oxygen ion mobility, via a mechanism analogous to that of the mobile lattice "holes" that allow electron flow in semiconductor materials, and the electrochemical oxygen ion flow is used to determine the oxygen gradient across the layer. A difference in partial pressures of oxygen across the wall induces a flow of oxygen ions between the electrodes, and the cell produces a voltage across the layer from which the ratio of the two partial pressures is determined.

By applying a reference gas of known oxygen content to one side of the sensor and admitting a sample gas from a process environment to the other side, the level of oxygen in the process environment may be derived from the magnitude of this voltage. However, owing to manufacturing and other variations in layer thickness and surface effects, various corrections in the form of bias offsets or factors of proportionality may be necessary, both initially and as the sensor ages, in order to convert this signal to an effective measurement of the prevailing oxygen level. Moreover, such sensors are generally not amenable to usage in dirty environments or in a gas environment that evolves quickly, such as a flue gas measurement environment.

Certain constructions have been proposed for generating an internal reference, so that the sensor is able to calibrate itself using the available gas rather than requiring a known reference standard to be separately supplied. Sensor systems of this type have been described by C. Franx, in Sensors and Actuators, Vol. 7, No. 4 (August, 1985), pp. 263–270, and by D. M. Haaland in Analytical Chemistry, Vol. 49, No. 12 (October, 1977), pp. 1813–1817. A typical such system employs two identical $ZrO_2$ disks, each with platinum electrode faces on both sides, and attaches the disks to opposite ends of a platinum or ceramic cylinder or spacer ring such that the disks form opposed end walls of a sealed cannister-like chamber. One of the two disks is operated as a standard $ZrO_2$ oxygen sensor, which, according to the Nernst equation, provides a signal which is a function of the $O_2$ partial pressures within and outside of the chamber. The other is connected with a reverse bias to operate as an electrochemical oxygen ion pump and to pump the interior of the chamber down to zero oxygen pressure between measurements. Assuming that the actual volume of the chamber is first determined, and preferably after first performing a factory reference calibration to develop a meter factor and determine a Nernst offset, the sensor may be subsequently re-zeroed in the field by a pumpdown procedure without requiring a separate span gas to be provided for reference. The internally referenced sensor operation of these devices may be useful for measuring oxygen levels provided that the sensor response time is sufficiently short compared to the time scale on which the sample gas fluctuates.

The foregoing construction has the disadvantage, however, that the process for assembly of the chamber bounded by two zirconia disks requires passage of two wires from the interior to the outside of the chamber, and of course also requires sealing the spacer ring in a leak-proof manner around the entire periphery of its top and bottom to the two disks which constitute the major active transport and measurement surfaces of the device. The overall construction presents a relatively large surface area, but this is achieved in a construction that requires two long narrow sealing junctions, about the peripheries of both disks, and is therefore vulnerable to small leaks which can shift measurement values during or between readings. These factors can impair the achievable levels of manufacturing quality, or can lead to increased development of micro-leaks once the sensor is put into service, and thus may require frequent recalibration.

It is therefore desirable to provide an improved oxygen sensor and method of determining oxygen level with an internal reference.

It is further desirable to provide such a sensor having decreased susceptibility to leakage.

It is also desirable to provide such a sensor having improved response characteristics.

SUMMARY OF THE INVENTION

These and other desirable features are provided in an oxygen sensor in accordance with the present invention, wherein a zirconium oxide body with a continuous inside face and a continuous outside face forms a thin shell enclosing a chamber of fixed volume. In discrete or separate time intervals, a controller in one time interval applies a signal across the two faces so that the sensor acts as an electrochemical oxygen ion pump, and in another time interval, alternately monitors the voltage produced by the oxygen ion current across the shell to determine the oxygen level. At each stage, the integrated pump current yields a measure of the oxygen added to or removed from the chamber. By pumping so that the chamber has been emptied, or has attained equilibrium with the outside, an internal calibration is achieved.

Preferably the shell is a tube with inner and outer surfaces electroded by respective layers of porous platinum, and the tube has length which is substantially greater than its diameter, and it is dependably sealed with an end plug through which a single electrode wire passes for connecting to the inner platinumized electrode surface. A suitable material for forming the sensor is a mixture of about 91% zirconium oxide and 9% yttrium oxide, and this material is formed or shaped as a paste or slurry into a single body to the final shell shape, e.g., a tube. The body is sintered at about 1400° C. to strengthen and set its shape, and the sintered body is then platinum coated to form porous electrodes on each surface. A lead is attached to the inner electrode surface and brought out through the open end of the tube, which is then sealed with a plug.

In a preferred mode of operation, a controller self-calibrates the sensor by energizing the electrode surfaces with a controlled flow of current at a first polarity to pump oxygen out of the chamber. Following a brief relaxation interval after pumping, a processor reads the cell output, and repeats the pumping and reading steps until it determines that the chamber is, as a practical matter, effectively empty. That is, the Nernst voltage indicates that the internal oxygen concentration is negligible with respect to the required measurement accuracy. This level may be, for example, about 200 mV for a typical flue gas application. The controller then switches polarity, and operates as an electrochemical oxygen ion pump in the reverse direction to fill the chamber to the prevailing oxygen concentration. In general, the amount of oxygen transported across the wall is directly proportional to the charge provided to the pump, so this procedure, when carried out in a gas of known oxygen concentration, calibrates the sensor. To operate as a pump and null the pressure difference across the sensor wall, a controller preferably reads the Nernst voltage, applies an amount of charge calculated to substantially achieve equilibrium, and then, after a relaxation time, again reads the Nernst voltage, repeating further pumping if necessary. The pumping current is preferably applied as a sequence of current pulses, and the ΔP Nernst cell output is read until the signal across the electrodes drops below noise threshold, indicating that $\Delta P_{oxygen}$ is effectively nulled. Preferably, the controller integrates the applied charge. For example, when applying fixed duration pulses of constant current, this is done by simply counting pulses and multiplying by a meter or conversion factor to determine the ambient oxygen level. Thereafter, as ambient fluctuates, the last reading may be stored in memory, and the controller may operate without the evacuation pump down step, to simply apply positive or negative pulses to maintain ΔP=0 so that the internal oxygen pressure tracks the current external oxygen pressure. The number of positive and negative pulses is then tallied in a running sum to determine the current equilibrium oxygen reading. Operation in a null-tracking mode in this manner effectively reduces leakage across the sensor even in the presence of micro-cracks or leak defects, so that the reading remains accurate for extended periods.

BRIEF DESCRIPTION OF DRAWINGS

These and other features of the invention will be understood from the description and claims herein, taken together with the drawings showing illustrative embodiments of the invention, wherein.

DETAILED DESCRIPTION

The method of the invention is described in greater detail below, in connection with a representative operating control circuit shown in FIG. 3. However one particular embodiment of a sensor adapted for the practice of the method will be first described.

Figure 1:
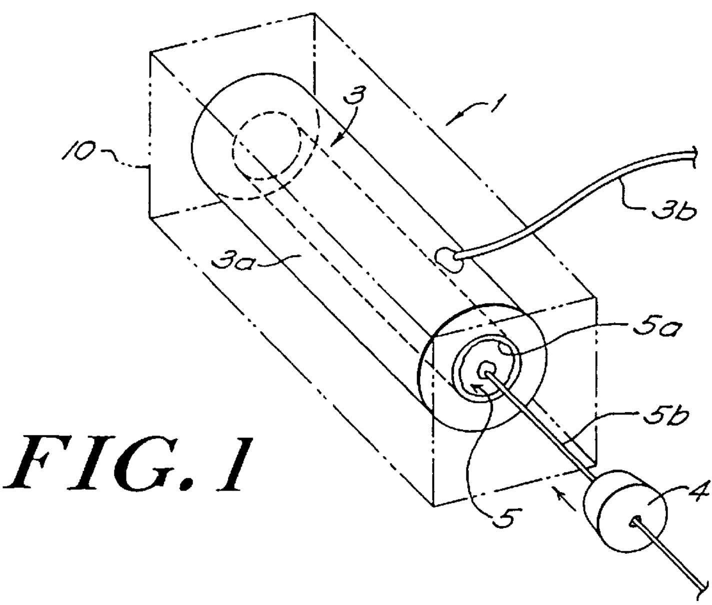
FIG. 1 shows a perspective view of a sensor in accordance with a first embodiment of the invention.

FIG. 1 shows one embodiment of an oxygen sensor 1 in accordance with the present invention. The sensor 1 includes and is primarily constituted by, a body of zirconium oxide which illustratively has been formed as a tube and constitutes an enclosure or chamber which is sealed, for example, by having a plug 4 closing its end. The body has an outer surface 3 and an inner surface 5 each of which has been metallized, for example, with a porous platinum coating, allowing the provision of electrical charge to or from the surfaces.

The technology for making electroded zirconia sheet oxygen sensors is well known, and will not be extensively described here. Basically, a paste of zirconium oxide is mixed with a minor percentage of yttrium oxide, is formed to shape as a sensor body and is then sintered at about 1400–1500° C. to strengthen and fix its structure. The surfaces of the sensor body are then metallized, for example, by coating with a platinum ink and baking out the carrier, to form outer and inner surfaces 3*a*, 5*a* which are each conductive. The platinum is porous, and in use, unless the intended sensing environment is itself a high temperature environment, the entire assembly is also operated within an oven 10, shown schematically, at a temperature above about 700° C. so that application of an electric field across the surfaces 3*a*,5*a* causes a flow of oxygen ions through the wall. Leads 5*b*, 3*b* are attached to the inner and outer surfaces 5 and 3, respectively for reading the electrical signal induced thereacross by the oxygen transport.

As shown, in this embodiment, one end of the tube is closed, either initially or by plugging an open cylinder tubular body, and the plug 4 closes the open end of the tube, while the lead 5*b* passes centrally through the plug, with appropriate sealing material, so that the interior of the tube is entirely closed off and separated from the outside. This construction uses only a single wire through-passage. In a prototype embodiment, the tube was fabricated to be twelve millimeters long by three millimeters outer diameter, with a one millimeter thick wall and an interior chamber depth of ten millimeters. A one millimeter diameter plug with a central hole closed the end of the chamber. For operation of the prototype, the sensor was placed in a small open-mouth furnace cavity of about fifteen millimeters depth, and was mounted together with the furnace on the tip of a probe or mounting assembly suitable for insertion in a stack or other plant location to measure flue gas.

The external surface area of the sensor was slightly under one square centimeter, and the internal chamber volume was about $7.5\times10^{-9}$ $m^3$ allowing the chamber to be emptied of oxygen quickly and re-filled in a short time by applying appropriate current pulses across the wall. Thus, the shell formed an enclosure of rapid response yet sufficiently large to resolve measurements with accuracy. A pump voltage between about 0.5–0.6 volts was found to be suitable, using a current in the range of 25–100 $\mu$A, and preferably about 40–50 $\mu$A. The applied charge was integrated to provide an exact measure of the amount of oxygen added to or removed from the chamber.

Figure 2B:
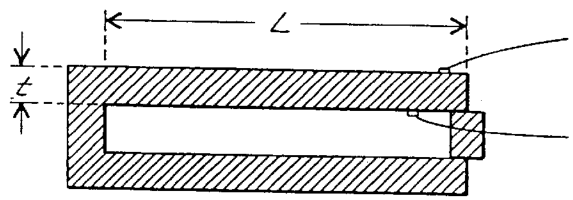
FIGS. 2A and 2B show a cross-sectional views through the sensor of FIG. 1 across its axis, and along its axis, respectively.
Figure 2A:
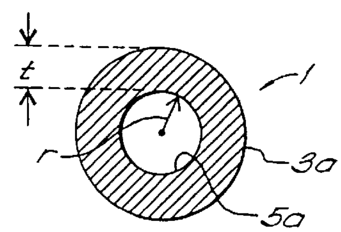

As shown in the cross-sectional views of FIGS. 2A and 2B, the sensor 1 of this embodiment has a length L and a lesser but substantially uniform wall thickness t, which for the prototype embodiment was about one millimeter. The annular cross section of the wall does not complicate the measurement of oxygen transport, and, so long as the applied voltage is kept sufficiently low as to not reduce the oxide material, typically below about 1.4 volts, the number of oxygen ions transported across the wall is given directly by the integrated current value, or charge. Furthermore, the tubular geometry provides a high surface area to volume ratio, so that the closed interior of the sensor is readily emptied, or its oxygen content adjusted, by the application of a continuous current or a sequence of current pulses within the above described voltage and current range, in a matter of seconds. Furthermore, the total interior volume is sufficiently large that a high degree of precision may be obtained with simple pumping sequences. This property is exploited to operate the sensor both as a pump, and allowing a suitable time interval for relaxation, as a battery to measure the achieved pressure differential.

In accordance with a further aspect of the invention, a complete system utilizes a controller which switches between an energizing regimen and a current-reading regimen, alternately applying pump pulses and reading measurements, and includes an integrator or counter to keep running track of the present level of oxygen. The controller may for example calibrate the cell by emptying it and thereafter filling it to a level such that the oxygen level matches that of atmospheric air or other standard. Alternatively, or in addition, the controller, having made one reference measurement or internal calibration, may continuously operate to track the surrounding oxygen concentration by achieving a null balance in which ΔP=0, while summing the pulses with their polarity, which have been applied to achieve or maintain this null balanced condition within the chamber.

Figure 3:
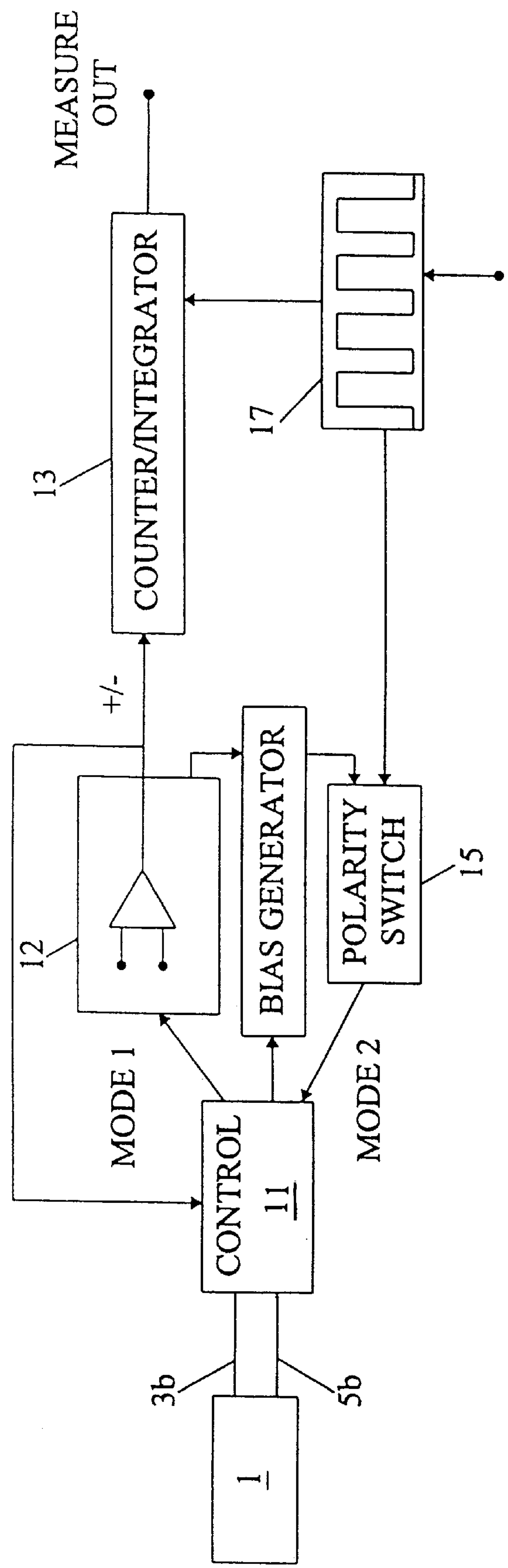
FIG. 3 illustrates a measurement system utilizing a sensor such as that of FIG. 1.

In a preferred mode of operation, the sensor is equipped with a control and processing system as shown in FIG. 3. In this system, the sensor cell 1 is alternately connected by the controller 11 in a first mode to a comparator 12 which amplifies the signal appearing at electrode lines 3*b*, 5*b* indicative of the difference in oxygen concentration on opposite sides of the sensor wall, or is connected in a second mode via a pole-reversing switch 15 to receive regular current pulses from a pulse generator or current source 17 to pump oxygen into or out of the interior. Following each pumping operation in the second mode, the controller sets a short time out or relaxation interval, then switches to the first mode to measure the present cell output, referred to simply as the ΔP output. For example, the controller may provide a one second delay when the sensor operates at 700 degrees Celsius to allow the signal from the pumping pulses to dies down, before reading the Nernst voltage. The necessary relaxation time increases with the level of the applied pumping signal, and decreases with higher temperature.

In implementing pumping to change the level of oxygen in the interior of the sensor, the controller may apply a simple stepped pumping sequence to quickly null the output, i.e., make ΔP=0. This may be done by applying pulses of an appropriate polarity at the maximum current or time duration when the magnitude of ΔP is greater than a first threshold, then reducing the pump rate to half-current or half-duration pulses when the magnitude of the ΔP output has dropped to a lesser level, and continuing this process until the ΔP output lies within the noise threshold of the sensor. This tracking operation may be implemented with a control chip, or with a simple analog circuit in which the cell output controls the applied current. Meanwhile, the applied current is integrated by a counter or integrator 13 to keep a running tally of the amount of oxygen which has been added to or removed from the sensor interior since its last pump down calibration. In the illustrated circuit, the polarity of the comparator output sets the direction of a bidirectional up/down counter, and the magnitude may be used to set a pulse height, width or bias. A typical operation sequence commences by applying pulses of a polarity to evacuate the cell interior while the cell resides in ambient air, and then operating to achieve ΔP=0 in ambient, so that integrated applied current together with the constant oxygen level of air together provide the required chamber volume and meter factors for subsequent operation. Thereafter, the running tally of in/out pumping current provides a direct measure of the surrounding oxygen level.

Preferably, once the cell has been calibrated to determine the proportionality between applied charge and change in internal oxygen level, and determine the correspondence between Nernst output voltage and the difference in level across the sensor wall, the controller may implement its tracking operation by reading the present Nernst output, converting this output to a pressure difference, and then applying a pump drive signal calculated to bring about the measured pressure difference inside the sensor so as to again null the output. The measured Nernst output may also be immediately applied to the most recent oxygen reading to update and display a new pressure value, even before the pumping and nulling operation commences. Thus the Nernst output is used as a feed forward signal to set the amount of the first pumping cycle for tracking the surrounding level, and to produce a hybrid output measurement based on the change from last reading. Subsequent pumping steps may be performed if necessary, following a relaxation interval and measurement of the Nernst output if this indicates that the signal has not been nulled or is no longer null.

Figure 5:
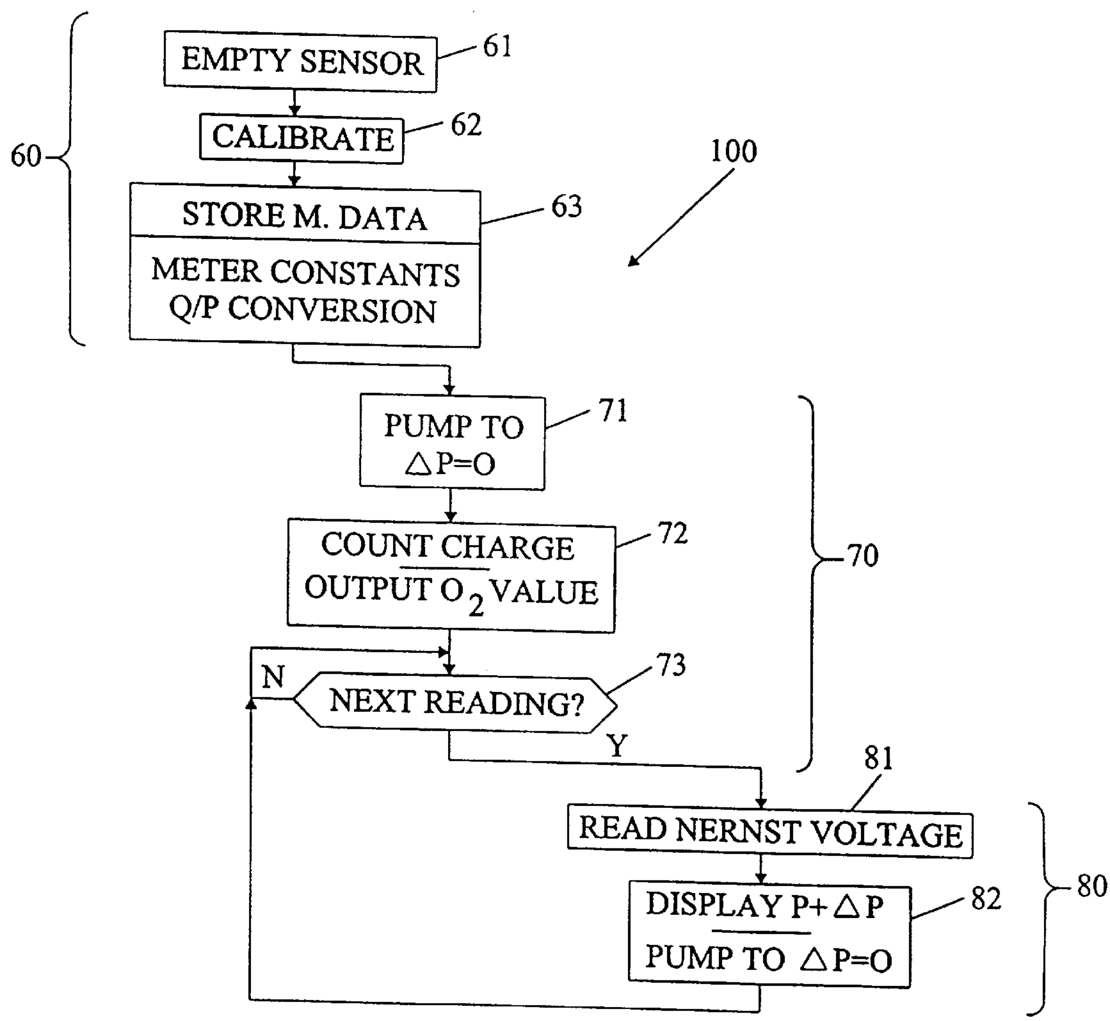
FIG. 5 is a flow chart illustrating aspects or stages of operation.

FIG. 5 illustrates representative steps of the methods 100 of operation and sensing of the present invention, aspects of which have been described above. The method includes a calibration stage 60, a stage 70 wherein the sensor is placed in operation in a measurement environment, and a stage 80 of continuing operation. The calibration is carried out by a step 61 of pumping out the interior, and one or more procedures to determine and store calibration data. Typically as described above this involves a calibrated filling step 62 wherein the cell is operated as a pump in a known oxygen environment while the pumping charge is integrated. This provides an absolute measure of cell volume, and determines any necessary constants which depend on the wall structure or material, so that any meter constants and charge/pressure conversion factors may be stored at step 63 as part of the initial cell or processor set-up. The same general steps may be initially performed in the field, emptying the cell and refilling it with a known reference, such as atmospheric air if recalibration becomes necessary. In any event, following initial calibration, the sensor is placed in duty by a sequence 71, 72 of counting charge as the evacuated cell is filled to equilibrium, and converting the measured pumping charge to an oxygen level reading using the stored meter characteristics. As noted above, the geometry of the preferred construction is highly immune to leaks, so if the cell is evacuated after initial calibration, it may not be necessary to evacuate it further at the start of this stage. However, initial evacuation is useful for confirming integrity of the wall and also observing the noise level and initiating the operating cycle. Since it involves no expense or inconvenience, this step is preferably also included in the start up cycle. Thereafter, measurement proceeds by determining if it is time to perform a new measurement (step 73), and then performing the continued measurement steps 81, 82 of the measurement cycle stage 80. The processor may be programmed to perform a measurement after a fixed time delay, such as once every two minutes, or it may read the Nernst output and proceed to perform a new measurement as soon as the output indicates that surrounding conditions have changed more than a threshold amount.

As noted above, the last reading results in the cell interior being placed in equilibrium with the surrounding oxygen level, i.e., ΔP=0, and the present reading is initiated at step 81 by reading the present Nernst voltage. In the preferred mode of operation the processor then adds the pressure difference indicated by the present differential reading to the last stored reading to provide an immediate oxygen level measurement value, and also determines the required pumping charge or pulse count to re-zero the Nernst output. Thus, the sensor system operates to always null the cell output, while immediately providing a running measure of oxygen level. This mode of operation eliminates much or all of the operational time involved in charge relaxation between the pumping and reading operations, and thus both expedites and extends the measurement capability of the sensor cell, especially when the oxygen level changes at a rate comparable to the intrinsic filling, null pumping and relaxation times.

The cell construction is highly immune to micro-leaks, and in this null-tracking mode of operation, the $O_2$ difference is kept close to zero for most of the time when the sensor is in operation. Thus, even if leaks occur, there is no driving differential and the change in interior oxygen levels due to leakage may be disregarded. The described method of operation therefore greatly reduces the need for field calibration. However the construction also lends itself to quick and accurate recalibration in the field by the self-reference pump down and refilling mode of operation described above.

For such internal calibration operation, applicant contemplates that the sensing cell preferably be incorporated in or be operated with a system having an air source which is selectively applied by the controller to immerse the sensor while it resides in situ, for example, while still mounted in a stack, for effecting a reference measurement. The reference measurement may be made as a first step of the normal measurement protocol, or may be made more infrequently, to correct for slow changes such as surface deposits, material degradation or leakage that may require an offset or scale correction.

Figure 4:
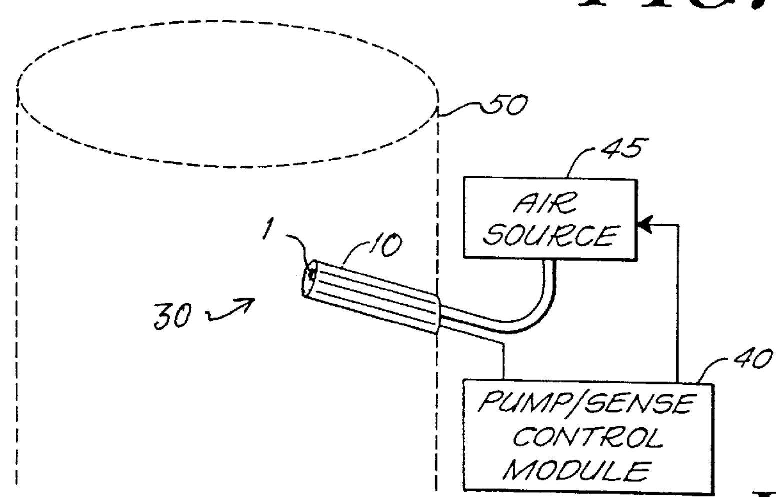
FIG. 4 illustrates a stack mount system using the internally calibrated sensor of FIG. 1.

FIG. 4 shows one such system 30. As shown therein, a sensing cell 1 as described above together with its oven 10 are mounted in a probe body 25 which extends into the gas stream of a stack 50 such as a power plant smokestack. The probe body 50 positions the cell in the sensing environment, and provides a slightly baffled mounting in which the sensor itself is protected from the direct flow of material moving up the stack. The probe body may itself be retractable, with an actuator such as an electrical or fluid actuated positioning assembly for advancing the tip into the stack gas, or may be a fixed assembly. A pumping/sensing control module as described above in connection with FIG. 3 is connected to the sensor cell by circuit leads extending through the probe, and is also connected to control an air source 45 mounted at the outboard side of the probe. The air source 45 is mounted to supply a flow of air through the probe body to the sensor/oven assembly so that the sensor will be immersed in normal atmospheric air when the source is actuated by the controller, and the controller is equipped for this purpose with a switch that is selectively actuated during an evacuation/refill calibration mode, allowing the controller to perform the above-described internal reference calibration during normal operation of the sensor in the stack 50.

For operation of the system 30 as described above, it is only necessary that the air source 45 intermittently supply a sufficient flow of reference air to temporarily prevent the stack gas from entering the baffled sensing oven. A valved vessel of pressurized air or other reference gas or mixture will suffice to provide the required reference for an extended period of operation. Preferably, however, this condition is implemented passively, relying on the presence of surrounding air or using a simple fan assembly to provide the required airflow through the oven. It is also contemplated that the probe tip may be positioned in the stack such that the Bernouilli pressure drop cause by flowing stack gas passively draws air from outside the stack, through the probe past the sensor, to provide the reference gas. In that case, a simple flap valve may be operated to selectively allow air ingress during the calibration step. Thus, rather than requiring a calibrated span gas, the field calibration is effected simply using atmospheric oxygen.

This completes a description of a basic embodiment and certain preferred implementations of sensor cells and measurement systems of the present invention.

However the invention contemplates other embodiments wherein the sensor body has a different form or shape defining an effective interior chamber, and also embodiments wherein a heater element is fabricated in the sensor body itself, optionally with one or more thermal sensing elements, obviating the need for an external oven. The invention being thus disclosed and described, further variations and modifications thereof will occur to those skilled in the art, and all such variations and modifications are considered to be within the scope of the invention, as set forth in the claims appended hereto and equivalents thereof.

What is claimed is:

1. An oxygen sensor including a sensor body comprising a zirconium oxide wall forming an empty shell about a close chamber and having an inner face and an outer face, said inner face and outer face having an inner and an outer porous conductive coating, respectively, effective for establishing inner and outer equipotential surfaces at said inner and said outer faces, a conductor passing externally of said closed empty chamber and connecting to said inner face to electrically communicate therewith and thus to register or to define a difference in oxygen level across the thickness dimension of the shell, said zirconium oxide wall and porous conductive coatings being configured to effectively pump oxygen across said wall to track changing oxygen concentration in a sample of unknown concentration being measured whereby by applying charge to said electrodes the shell operates as an electrochemical pump and by detecting potential across said electrodes the shell operates as a Nernst cell for effective calibration and measurement of oxygen level at said outside surface, and a control circuit attached to said porous conductive coatings and configured to establish a reference level of oxygen in said chamber and thereafter with the sensor in a measurement environment, to detect a potential difference and to apply a signal to pump oxygen in or out of said chamber so as to substantially continuously equalize the level of oxygen in said closed chamber with the level of oxygen at said outside surface, whereby leakage due to difference in pressure across said wall is negligible and measurement accuracy is maintained for an extended time without recalibration.

2. An oxygen sensor according to claim 1, wherein said zirconium oxide shell forms a tube defining said chamber.

3. An oxygen sensor according to claim 2, wherein the tube has a length L and a radius r, and wherein $L>>r$.

4. An oxygen sensor according to claim 3, wherein a plug seals an end of said tube, and wherein the conductor electrically connects to the conductive coating of the inner face via said plug.

5. An oxygen sensor according to claim 2, wherein said control circuit is configured to perform a first step of establishing an electrochemical ion current between inner and outer faces to transport oxygen across the shell, and to perform a second step of detecting a signal between the inner and the outer faces, said circuit repeatedly performing said first and second steps in alternating time intervals.

6. An oxygen sensor according to claim 2, further comprising a control circuit operative in a first mode to apply current to said conductor for pumping oxygen across the shell for establishing a level of oxygen in the closed chamber; and operative in a second mode for reading voltage across the shell to perform a measurement.

7. An oxygen sensor according to claim 6, further wherein said control circuit is operable to apply current reversibly in said first mode, and applies said current first in one direction to pump oxygen across the wall for establishing a zero reference level, and thereafter applies current in a direction effective to pump oxygen across the wall for establishing a zero differential level.

8. An oxygen sensor according to claim 7, wherein said control circuit operates in said second mode between steps of pumping oxygen in said first mode and, responsive thereto, controls steps of said first mode to achieve said zero reference of said zero differential level.

9. An oxygen sensor according to claim 8, wherein said control circuit further comprises means for integrating charge applied in said first mode to provide an absolute measurement of oxygen.

10. An oxygen sensor according to claim 9, further comprising a memory for storing a preceding measurement, whereby the charge integration means determines a current measure of oxygen level from said preceding measurement without performing a zero-reference measurement.

11. An oxygen sensor according to claim 6, wherein said control circuit receives the Nernst voltage as a feedforward signal and, responsive thereto, applies an estimated amount of charge estimated to quickly reduce oxygen pressure difference across the shell and substantially null the Nernst voltage.

12. A method of calibrating an oxygen sensor for measurement of oxygen level, such method comprising the steps of:

providing a zirconium oxide wall forming an empty shell which is sealed by a closing means and having an inner surface and an outer surface, wherein the inner surface and the outer surface are provided with respective first and second electrodes, and (i) during a first time applying a current across said first and second electrodes to effect electrochemical oxygen ion transport through said wall, and (ii) during a second time reading voltage across said first and second electrodes to determine and oxygen differential across said wall, said first and second times being separate, and said step of applying a current being performed to either remove substantially all oxygen from said sealed enclosure or to achieve ambient oxygen level in said sealed enclosure, wherein the steps of applying a current and reading a voltage are carried out to first substantially empty interior oxygen from the sealed enclosure and subsequently to substantially equalize said interior oxygen with an external reference gas thereby calibrating the sensor.

13. The method of claim 12, wherein the method includes the step of temporarily providing said reference gas about the outside of said sealed enclosure.

14. The method of claim 13, wherein the reference gas is normal atmospheric oxygen.

15. The method of claim 14, wherein the step of temporarily providing is performed by providing said reference gas while the zirconium oxide sealed enclosure remains mounted in a measurement environment.

16. The method of claim 12, wherein the method is carried out to maintain a substantially null difference in oxygen levels across the wall as the external oxygen level varies so that microleaks do not change oxygen level and impair accuracy of said reading.

17. A method of operating an oxygen sensor of the ion transport type, such method being characterized by the steps of calibrating a sensor having a zirconium oxide wall forming an empty shell and being closed to form a sealed chamber, and thereafter when the sensor is placed in a surrounding sample having an unknown or changing oxygen level, detecting a Nernst voltage across the wall and responsive thereto applying charge to the wall to operate the sensor as an electrochemical ion pump so as to maintain a substantially continuously null oxygen level difference across the sensor wall between oxygen level inside the sealed chamber and oxygen level in said surrounding sample, thus effectively eliminating net leakage and maintaining sensor accuracy for an extended period without recalibration.

18. The method of claim 17, wherein the step of calibrating is performed by measuring charge required to fill the sensor with atmospheric oxygen.

19. The method of claim 17, wherein the step of maintaining a substantially null oxygen level difference is performed by the steps of i) reading a Nernst voltage indicative of oxygen level difference ii) applying an amount of charge effective to transport oxygen across the sensor to largely reduce the difference, and iii) repeating steps i) and ii) to effectively null the difference whereby the sensor tracks ambient pressure with few reading iterations thereby enhancing response time.

20. The method of claim 17, further comprising the step of summing net charge applied to the sensor and converting said net charge to a measure of the current oxygen level.

* * * * *